United States Patent [19]

Pullen et al.

[11] Patent Number: 5,328,682
[45] Date of Patent: Jul. 12, 1994

[54] MOUTHWASH

[75] Inventors: John H. Pullen; Rabinder Singh; Kathryn A. Phillips, all of Nottinghamshire, England

[73] Assignee: Boots Company plc, England

[21] Appl. No.: 39,392

[22] PCT Filed: Oct. 19, 1991

[86] PCT No.: PCT/EP91/01986
§ 371 Date: Apr. 21, 1993
§ 102(e) Date: Apr. 21, 1993

[87] PCT Pub. No.: WO92/07547
PCT Pub. Date: May 14, 1992

[51] Int. Cl.⁵ .............................. A61K 7/16
[52] U.S. Cl. ...................................... 424/49
[58] Field of Search ..................... 424/49–58

[56] References Cited

U.S. PATENT DOCUMENTS

| | | |
|---|---|---|
| 3,506,757 | 4/1970 | Salzmann . |
| 3,683,065 | 8/1972 | Lauster . |
| 3,903,261 | 9/1975 | Miyoshi et al. ........... 424/56 |
| 3,935,307 | 1/1976 | Aimoto et al. ........... 424/56 |
| 3,966,863 | 6/1976 | Forward et al. . |
| 3,995,024 | 11/1976 | Hawking et al. ........ 424/55 |
| 4,029,760 | 6/1977 | De Roeck ................ 424/48 |
| 4,066,745 | 1/1978 | Tomlinson et al. ...... 424/49 |
| 4,075,317 | 2/1978 | Mitchell et al. . |
| 4,108,978 | 8/1978 | Mazzanobile et al. ..... 424/49 |
| 4,329,448 | 5/1982 | Cox et al. ............... 536/123 |
| 4,391,798 | 7/1983 | Tavss et al. ............. 424/52 |
| 5,178,869 | 1/1993 | Ebine et al. ............ 424/401 |
| 5,188,821 | 2/1993 | Gaffar et al. ........... 424/52 |

FOREIGN PATENT DOCUMENTS

| | | | |
|---|---|---|---|
| 346097 | 12/1989 | European Pat. Off. | ......... 424/49 |
| 517319 | 12/1992 | European Pat. Off. | ......... 424/49 |
| 543442 | 5/1993 | European Pat. Off. | ......... 424/49 |
| 728243 | 4/1955 | United Kingdom . | |
| 8911848 | 12/1989 | World Int. Prop. O. . | |

OTHER PUBLICATIONS

WPI File Supplier, Derwent Publications Ltd, AN-80-57547, & JP, A, 55085513, 28 Jun. 1980.

Primary Examiner—Shep K. Rose
Attorney, Agent, or Firm—Ostrolenk, Faber, Gerb & Soffen

[57] ABSTRACT

Abrasive mouthwash compositions suitable for a "rinse and brush" type product are described and are broadly defined as a pourable suspension containing the following essential components:
a) 0.1–50% abrasive e.g. silica;
b) 0.01–5% suspending agent e.g. montmorillonite clay;
c) 0.1–5% surfactant e.g. sodium lauryl sulphate and
d) liquid carrier e.g. water and humectant.

Optional further components include flavourings, colourings, anti-plaque agents, anti-tartar agents, agents for sensitive teeth, fluoride ion sources and sweeteners.

23 Claims, No Drawings

MOUTHWASH

The present invention relates to oral hygiene compositions, and in particular to mouthwash compositions.

Oral hygiene compositions fall into two main categories: dentifrices and mouthwashes. Dentifrices generally contain an insoluble dentally acceptable abrasive which is utilised to physically cleanse the surface of the teeth. Dentifrices are generally provided in the form of solid or pasty preparations which can be readily applied to a toothbrush, for example, powders, pastes or viscous gels.

Mouthwash compositions known hitherto generally comprise solutions containing small amounts of colourings, flavourings and antibacterial or other active ingredients. These solutions have found use as breath-freshening, antiseptic and/or anti-plaque mouthrinses or gargle preparations and are commonly used in addition to conventional tooth cleansing dentifrices.

Whilst mouthwashes and abrasive dentifrices have been produced as separate products for many years, it has not hitherto been suggested that a satisfactory form of combined product could be prepared in which an effective amount of abrasive could be maintained in an organoleptically acceptable stable suspension having a sufficiently low viscosity to be used as a mouthwash preparation.

The present invention provides an abrasive mouthwash composition which comprises
a) 0.1 to 50% by weight of dentally acceptable abrasive;
b) 0.01 to 5% by weight of synthetic or natural clay;
c) 0.1 to 5% by weight of surfactant; and
d) at least 45% of a liquid carrier, in the form of a pourable suspension having a viscosity (Brookfield) in the range of 1 to 2000 cps.

Surprisingly, the invention provides mouthwash compositions containing an effective amount of abrasive maintained in a substantially stable suspension having a sufficiently low viscosity to be used as a mouth rinsing preparation. Preferably the pourable suspensions have a viscosity in the range of 1 to 2000 cps, more preferably 20 to 1500 cps, particularly 100 to 1000 cps e.g. 200 to 600 cps (measured on a Brookfield LVT viscometer at speed 12 with spindle LV3). The mouthwash compositions according to the invention have a mildly abrasive action on the teeth when rinsed around in the mouth and as such can be utilised by the consumer as an "easy-to-use" convenience product to replace conventional mouthwashes and dentifrices. Preferably, the novel mouthwashes are used, in conjunction with a toothbrush, to thoroughly cleanse the teeth by the combined action of abrasive and toothbrush, thereby providing a combined "rinse and rush" product. If desired, the abrasive mouthwashes may also be used in a conventional manner as pre- or post-brushing rinses which have excellent teeth cleansing and mouth freshening properties.

In the preferred practice of the invention, an abrasive mouthwash as herein described is used regularly, preferably 1 to 3 times daily, in place of a conventional dentifrice. A typical usage involves rinsing the mouth with, for example, 5 to 10 ml of the composition, expelling the bulk of the composition from the mouth, brushing the teeth with a toothbrush and finally re-rinsing the oral cavity with a further 5 to 10 ml of either mouthwash or water. It has been found that sufficient composition remains in the mouth after expulsion to give a satisfactory foaming and abrasive action, when used in conjunction with a toothbrush, and to provide a long-lasting fresh mouthfeel after use.

Typical dentally acceptable abrasives include insoluble calcium salts such as calcium carbonate, available commercially for example under the trade name Sturcal (Sturge), and various calcium phosphates, alumina, silica, synthetic resins and mixtures thereof. Suitable dentally acceptable abrasives may generally be defined as those having a radioactive dentine abrasion value (RDA) of from about 30 to about 200 at the concentrations used in the compositions of the present invention. Preferred abrasives are non-crystalline silica abrasives, particularly in the form of precipitated silica or milled silica gels available commercially for example under the trade names Zeodent (Zeofinn OY) and Syloblanc (Grace) respectively. Preferred compositions according to the invention comprise 1 to 20%, more preferably 4% to 15% by weight of silica abrasive.

The mouthwashes according to the invention also contain at least one suspending agent which maintains the solid abrasive particles in a substantially stable suspension during storage without over-thickening the composition. Suitable suspending agents include synthetic and natural clays such as smectite and montmorillonite clays, available commercially for example under the trade names Laponite (Laporte Industries), Veegum (R. T. Vanderbilt) and Gelwhite (English China Clays), polysaccharide gums preferably anionic gums such as carboxymethylcellulose and xanthan, available commercially for example under the trade name Rhodigel (Rhone Poulenc), polymers such as acrylic acid polymers available commercially for example under the trade names Carbopol (B. F. Goodrich) and Dispex (Allied Colloids), and mixtures thereof. A suitable mixture comprises a mixture of an anionic gum and a clay, for example a mixture of xanthan gum and smectite clay in a ratio of approximately 1:1, suitable compositions comprising 0.1 to 1% of this mixture. It will be apparent to a person skilled in the art of preparing oral hygiene compositions that the amount of suspending agent required will depend, in part, on the nature of the suspending agent used and the relative amounts and natures of the abrasive and liquid carrier utilised. However, preferred compositions comprise 2 to 5%, more preferably 3 to 4% by weight of a suspending agent, preferably montmorillonite clay. In an especially preferred composition, the suspending agent comprises 3.3–3.7% of a montmorillonite clay, for example 3.5%.

Surfactants (surface active agents) are incorporated into the abrasive mouthwashes of the present invention to aid wetting, to improve the cleansing capability of the compositions, to produce a cosmetically acceptable foam in use, and to solubilise flavouring oils when present. Suitable surfactants include conventional anionic, nonionic and amphoteric surfactants and mixtures thereof. Anionic surfactants such as sodium methyl cocoyl taurate and higher alkyl sulphates, especially sodium lauryl sulphate available commercially for example under the trade name Empicol LZ (Albright & Wilson), are generally preferred. However, certain compositions particularly those containing cationic active ingredients, preferably contain nonionic surfactants such as block copolymers for example ethylene oxide and propylene oxide copolymers e.g. Poloxamer 184, ethoxylated hydrogenated castor oils available commercially for example under the trade name Croduret (Croda), and ethoxylated sorbitan esters available commercially for example under the trade name Tween (ICI). Preferred compositions comprise 0.2 to 2.5% by weight of surfactant.

Mouthwash compositions according to the invention may comprise at least 45%, preferably at least 60%, more preferably 80 to 99%, most preferably 80 to 90% by weight of liquid carrier but it will be understood that this proportion depends to a large extent on the proportion of abrasive incorporated into the composition. The liquid carrier may be in the form of a solution, emulsion or microemulsion of components and generally contains at least 5% by weight of water, preferably at least 10% by weight of water. Alcohol such as ethanol may optionally form part of the liquid carrier, for example 5 to 35% by weight of the liquid carrier, and is particularly preferred in mouthwash compositions having a high flavour impact and breath-freshening and/or antiseptic properties.

The liquid carrier desirably contains a humectant to enhance the mouthfeel of the product and to prevent drying out. Typical humectants include glycerin, sorbitol and glycols such as propylene glycol and polyethylene glycol, and mixtures thereof. Alternatively or in addition to humectant, the liquid carrier may contain silicone oils, for example, in an amount of 0.1 to 5% by weight. In clear products where the refractive index is an important consideration, silica is the preferred abrasive and the liquid carrier preferably comprises at least 86% by weight of sorbitol or at least 70% by weight of glycerin or a corresponding mixture thereof.

The mouthwashes of the present invention generally contain flavouring agents commonly in the form of oils commercially available as mouthwash and toothpaste flavours. Typical flavouring agents include peppermint, spearmint, aniseed, menthol, eucalyptus, clove, thymol and wintergreen, and mixtures thereof. High levels of flavouring oils can be incorporated into the mouthwashes of the invention by forming an emulsion in the liquid carrier. This is particularly advantageous in mouthwashes which are required to have little or no alcohol content but which need to have a high flavour impact. Conventional mouthwashes containing high flavouring concentrations generally utilise substantial levels of alcohol to dissolve the flavouring oils. High flavouring content is also desirable in mouthwashes which contain an unpleasant tasting active ingredient, for example an agent to reduce tooth sensitivity such as strontium chloride or an anti-tartar agent such a tetrapotassium pyrophosphate salts. The preferred abrasive mouthwashes according to the invention contain 0.1 to 1.5%, preferably 0.2 to 1% by weight of flavouring agent.

Advantageously, the compositions of the invention further comprise an active ingredient having anti-plaque activity. Suitable anti-plaque agents include non-ionic antibacterial agents such as bromochlorophene and triclosan and cationic agents such as cetylpyridinium chloride and chlorhexidine salts. In general, non-ionic antibacterial agents have a very low solubility in water and have not been incorporated into mouthwash preparations other than those containing high levels of alcohol. Furthermore, it is known that certain water-insoluble flavouring oils such as anethole and menthol have an antibacterial effect at high concentrations. A major advantage of the abrasive mouthwashes described herein is that a water-insoluble antibacterial agent and/or a water-insoluble anti-tartar agent may be incorporated into non-alcoholic mouthwashes at effective levels, in the form of an emulsion or suspension. Preferred abrasive mouthwash compositions comprise 0.001 to 1%, more preferably 0.01 to 0.5% by weight of a non-ionic antibacterial agent. Suitable water-insoluble anti-tartar agents comprise zinc salts, preferably zinc citrate. Preferred abrasive mouthwash compositions comprise 0.1 to 1% of a water-insoluble anti-tartar agent.

The compositions of the invention commonly incorporate colourings, which may be soluble colouring agents conventionally used in mouthwashes or may be insoluble colour pigments or whitening agents such as titanium dioxide, pearlising agents such as mica, or mixtures thereof. Colour pigments are generally available in a wider range of colours and are less susceptable to fading than soluble colouring agents and may therefore be used to advantage in the novel mouthwashes of the invention.

The pH of the mouthwashes according to the invention is generally in the range of from about 3.5 to about 9.0 and is typically from about pH 5.5 to pH 8.0. If desired, pH can be controlled with acid, for example citric acid, or base, for example sodium hydroxide, or buffered, for example with citrate, phosphate or bicarbonate buffering salts.

Various other materials may be incorporated into the mouthwashes of the present invention which will be well known to those skilled in the art. These include, for example, sweeteners such as saccharin and aspartame; preservatives such as sodium benzoate and parabens; fluoride ion sources such as sodium fluoride, sodium monofluorophosphate and amine fluorides (for example 1–1500 ppm of fluoride ion; preferably 200–1000 ppm of fluoride ion); anti-tartar agents such as water-soluble pyrophosphate salts, preferably alkali metal pyrophosphates; agents which reduce tooth sensitivity including potassium salts such as potassium nitrate and potassium chloride (for example 1 to 5% by weight) and strontium salts such as strontium chloride and strontium acetate (for example 2 to 10% by weight); and vitamins such as vitamin A. These optional additives may together comprise 0.1 to 10%, preferably 0.5 to 5% by weight of the composition.

Suitable abrasive mouthwash compositions according to the invention are compositions which may require shaking prior to use but which provide stable suspensions during use.

The preferred abrasive mouthwash compositions according to the invention are pourable, pleasant tasting suspensions which remain physically stable after storage, preferably after long-term storage for example for over 3 months, at ambient temperatures and in particular have suitable sedimentation times, for example, greater than 3 months. In one preferred embodiment of the invention, an abrasive mouthwash composition comprises:

a) 4 to 15% by weight of silica abrasive;
b) 3.0 to 4.0% by weight of suspending agent, preferably in the form of a montmorillonite clay;
c) 0.2 to 2.5% by weight of surfactant, preferably a higher alkyl sulphate;
d) 80 to 95% by weight of liquid carrier, preferably comprising a mixture of water and 5 to 15% by weight of the composition of humectant; and
e) 0.2 to 1% by weight of flavouring, in the form of a pourable suspension having a viscosity (Brookfield) of 1 to 2000 cps.

A further advantage of the abrasive mouthwashes according to the invention is their ease of manufacture compared to the manufacture of conventional dentifrices such as toothpastes. It is well known in the art that stringent production methods are required to obtain a satisfactory toothpaste product, for example manufacture must be carried out under vacuum to prevent the formation of air bubbles which produce a visually unacceptable product and may lead to oxidation of the flavourings and syneresis of the product. In contrast, abrasive mouthwashes are easily formulated by dispersing the abrasive into a mixture of surfactant, suspending agent and liquid carrier, under normal production conditions without the use of vacuum facilities.

Yet another advantage of the preferred abrasive mouthwashes according to the present invention is their surprisingly improved bactericidal activity. Preferred compositions of the present invention show excellent in vitro bactericidal activity against *S. Salivarius* even when the anti-bacterial agent, bromochlorophene, is present in as low a concentration as 0.01%.

The abrasive mouthwash compositions according to the invention are illustrated by the following Examples. The flavours were added by volume (v).

EXAMPLE 1

|  |  | % w/v |
|---|---|---|
| 1) | Glycerin | 10 |
| 2) | Xanthan gum (sold under the trade name Rhodigel 23) | 0.12 |
| 3) | Sodium lauryl sulphate (sold under the trade name Empicol LZ) | 1.0 |
| 4) | Silica (sold under the trade name Zeodent 113) | 10 |
| 5) | Titanium dioxide (sold under the trade designation B.P.) | 0.1 |
| 6) | Sodium saccharin | 0.1 |
| 7) | Flavour | 0.6 v |
| 8) | Water | ad. 100 |

Component 2 was thoroughly dispersed in component 1. Approximately 70% of the water was slowly added to the mixture with continual stirring and components 3 and 6 dissolved therein. Components 4 and 5 were evenly dispersed into the mixture with stirring, component 7 added and the mixture made up to 100% with water to give the abrasive mouthwash of Example 1.

EXAMPLE 2

|  |  | % w/v |
|---|---|---|
| 1) | Glycerin | 10 |
| 2) | Xanthan gum (sold under the trade name Rhodigel 23) | 0.15 |
| 3) | Sodium lauryl sulphate (sold under the trade name Empicol LZ) | 1.0 |
| 4) | Silica (sold under the trade name Zeodent 113) | 10 |
| 5) | Sodium saccharin | 0.1 |
| 6) | Flavour | 0.5 v |
| 7) | Colour | 0.001 |
| 8) | Water | ad. 100 |

Components 1 to 8 were formulated in a manner analogous to that described in Example 1 to give the abrasive mouthwash of Example 2.

EXAMPLE 3

|  |  | % w/v |
|---|---|---|
| 1) | Glycerin | 10 |
| 2) | Xanthan gum (sold under the trade name Rhodigel 23) | 0.2 |
| 3) | Smectite clay (sold under the trade name Veegum D) | 0.2 |
| 4) | Sodium lauryl sulphate (sold under the trade name Empicol LZ) | 1.0 |
| 5) | Silica (sold under the trade name Zeodent 113) | 10 |
| 6) | Sodium saccharin | 0.1 |
| 7) | Bromochlorophene | 0.1 |
| 8) | Flavour | 0.3 v |
| 9) | Sodium fluoride | 0.05 |
| 10) | Colour | 0.001 |
| 11) | Water | ad. 100 |

Xanthan gum (component 2) was thoroughly dispersed in glycerin (component 1). Clay (component 3) was thoroughly dispersed in approximately 70% of the water and the aqueous mixture was slowly added to the non-aqueous dispersion of gum with continual stirring. Soluble components 4, 6, 9 and 10 were dissolved in the mixture and component 5 was evenly dispersed therein with stirring. Bromochlorophene (component 7) was dissolved in the flavour (component 8) and added to the bulk. The mixture was made up to 100% with water to give the abrasive mouthwash of Example 3.

EXAMPLE 4

|  |  | % w/v |
|---|---|---|
| 1) | Glycerin | 10 |
| 2) | Xanthan gum (sold under the trade name Rhodigel 23) | 0.3 |
| 3) | Smectite clay (sold under the trade name Veegum D) | 0.3 |
| 4) | Sodium lauryl sulphate (sold under the trade name Empicol LZ) | 1.0 |
| 5) | Calcium carbonate (sold under the trade name Sturcal H) | 10 |
| 6) | Sodium saccharin | 0.1 |
| 7) | Bromochlorophene | 0.1 |
| 8) | Sodium monofluorophosphate | 0.17 |
| 9) | Flavour | 0.3 v |
| 10) | Colour | 0.001 |
| 11) | Water | ad. 100 |

Components 1 to 11 are formulated in a manner analogous to that described in Example 3 to give the abrasive mouthwash of Example 4.

EXAMPLE 5

|  |  | % w/v |
|---|---|---|
| 1) | Glycerin | 10 |
| 2) | Xanthan gum (sold under the trade name Rhodigel 23) | 0.2 |
| 3) | Ethoxylated sorbitan ester (sold under the trade name Tween 20) | 1.0 |
| 4) | Silica (sold under the trade name Zeodent 113) | 10 |
| 5) | Sodium saccharin | 0.1 |
| 6) | Sodium fluoride | 0.05 |
| 7) | Potassium chloride | 1.0 |
| 8) | Flavour | 0.3 v |
| 9) | Colour | qs |
| 10) | Water | ad. 100 |

Components 1 to 10 are formulated in a manner analogous to that described in Example 3 to give the abrasive mouthwash of Example 5.

EXAMPLE 6

| | | % w/v |
|---|---|---|
| 1) | Glycerin | 10 |
| 2) | Xanthan gum (sold under the trade name Rhodigel 23) | 0.3 |
| 3) | Ethoxylated sorbitan ester (sold under the trade name Tween 20) | 1.0 |
| 4) | Silica (sold under the trade name Zeodent 113) | 10 |
| 5) | Sodium saccharin | 0.1 |
| 6) | Sodium fluoride | 0.05 |
| 7) | Potassium chloride | 1.0 |
| 8) | Tetrapotassium pyrophosphate | 0.75 |
| 9) | Tetrasodium pyrophosphate | 0.75 |
| 10) | Flavour | 0.5 v |
| 11) | Colour | qs |
| 12) | Water | ad. 100 |

Components 1 to 12 are formulated in a manner analogous to that described in Example 3 to give the abrasive mouthwash of Example 6.

EXAMPLE 7a

| | | % w/v |
|---|---|---|
| 1) | Glycerin | 10 |
| 2) | Montmorillonite clay (sold under the trade name Gelwhite HNF) | 3.5 |
| 3) | Sodium lauryl sulphate (sold under under the trade name Empicol LZ) | 0.5 |
| 4) | Silica (sold under the trade name Zeodent 113) | 10 |
| 5) | Sodium saccharin | 0.1 |
| 6) | Bromochlorophene | 0.1 |
| 7) | Sodium fluoride | 0.05 |
| 8) | Methyl paraben | 0.2 |
| 9) | Flavour | 0.3 v |
| 10) | Colour | 0.0005 |
| 11) | Water | ad. 100 |

Clay was dispersed in glycerin, 50% of the water added and the mixture was homogenised using a high shear mixer/homogeniser (Silverson) mixer for 10–15 minutes. Components 5, 7, 8 and 10 were dissolved in a small amount of water and mixed thoroughly into the clay dispersion. Components 3 and 4 were added and the mixture dispersed thoroughly. Component 6 was dissolved in the flavouring and added to the bulk. The mixture was made up to 100% with water to give the abrasive mouthwash of Example 7a. The initial viscosity was 500 cps.

EXAMPLE 7b

A large scale (1 ton) factory batch was prepared in a similar manner to Example 7a except that an in-line homogeniser was used. The initial viscosity was 350 cps.

EXAMPLE 7C

This was prepared as described in Example 7a but omitting the bromochlorophene.

EXAMPLE 8

| | | % w/v |
|---|---|---|
| 1) | Glycerin | 2.0 |
| 2) | Xanthan gum (sold under the trade name Rhodopol SC) | 0.2 |
| 3) | Smectite clay (sold under the trade name Veegum D) | 0.8 |
| 4) | Sodium polyacrylate (sold under the trade name Dispex N40) | 0.1 |
| 5) | Sodium lauryl sulphate (sold under under the trade name Empicol LZ) | 1.0 |
| 6) | Sorbitol (70%) | 8.0 |
| 7) | Silica (sold under the trade name Zeodent 113) | 10 |
| 8) | Alcohol (96%) | 10 |
| 9) | Sodium saccharin | 0.1 |
| 10) | Sodium fluoride | 0.05 |
| 11) | Bromochlorophene | 0.1 |
| 12) | Colour | 0.0004 |
| 13) | Flavour | 0.35 v |
| 14) | Methyl paraben | 0.1 |
| 15) | Propyl paraben | 0.1 |
| 16) | Water | ad. 100 |

Clay was dispersed in 50% water using Silverson mixer. Xanthan gum was dispersed in glycerin and thoroughly mixed into the clay mixture. Components 4, 9, 10, 12 and 14 were dissolved in a small amount of water and added to the clay mixture whilst mixing. Components 6 and 8 were added to the bulk and mixed until dispersed. Components 5 and 7 were added and mixed thoroughly. Components 11 and 15 were dissolved in the flavour and added to the bulk. The mixture was made up to 100% with water to give the abrasive mouthwash of Example 8. The initial viscosity was 950 cps.

EXAMPLE 9

| | | % w/v |
|---|---|---|
| 1) | Glycerin | 10 |
| 2) | Montmorillonite clay (sold under the trade name Gelwhite HNF) | 2.0 |
| 3) | Sodium lauryl sulphate (sold under under the trade name Empicol LZ) | 0.5 |
| 4) | Silica (sold under the trade name Zeodent 113) | 10 |
| 5) | Sodium saccharin | 0.1 |
| 6) | Bromochlorophene | 0.1 |
| 7) | Sodium fluoride | 0.05 |
| 8) | Methyl paraben | 0.2 |
| 9) | Flavour | 0.3 v |
| 10) | Colour | 0.0005 |
| 11) | Water | ad. 100 |

This Example was prepared as described in Example 7a.

EXAMPLE 10

| | | % w/v |
|---|---|---|
| 1) | Glycerin | 10 |
| 2) | Montmorillonite clay (sold under the trade name Gelwhite HNF) | 5.0 |
| 3) | Sodium lauryl sulphate (sold under under the trade name Empicol LZ) | 0.5 |
| 4) | Silica (sold under the trade name Zeodent 113) | 10 |
| 5) | Sodium saccharin | 0.1 |
| 6) | Bromochlorophene | 0.1 |
| 7) | Sodium fluoride | 0.05 |
| 8) | Methyl paraben | 0.2 |
| 9) | Flavour | 0.3 v |
| 10) | Colour | 0.005 |

-continued

|  | % w/v |
|---|---|
| 11) Water | ad. 100 |

This Example was prepared as described in Example 7a. The initial viscosity was 450 cps.

EXAMPLE 11

|  |  | % w/v |
|---|---|---|
| 1) | Glycerin | 10 |
| 2) | Montmorillonite clay (sold under the trade name Gelwhite HNF) | 3.4 |
| 3) | Sodium lauryl sulphate (sold under under the trade name Empicol LZ) | 1.0 |
| 4) | Silica (sold under the trade name Zeodent 113) | 10 |
| 5) | Sodium saccharin | 0.1 |
| 6) | Bromochlorophene | 0.1 |
| 7) | Sodium fluoride | 0.05 |
| 8) | Alcohol (96%) | 10.0 |
| 9) | Flavour | 0.3 v |
| 10) | Water | ad. 100 |

This Example was prepared as described in Example 8. The viscosity after 1 week was 1500 cps.

STABILITY TESTING

All samples were checked initially and, if no obvious visible signs of sedimentation had occurred, at 1 month, 2 months, 3 months and 6 months, with the following parameters measured each time:
1) appearance
2) taste
3) viscosity
4) sedimentation
5) pH
6) activity testing (fluoride and bromochlorophene)
7) preservation at initial and 6 months All the Examples had acceptable appearance, taste, viscosity and pH.

Sedimentation was measured by taking 3 different aliquots of product from the top, middle and bottom of each bottle and applying the above tests. The sedimentation test mentioned above gives a fairly accurate indication of the silica content in each aliquot and is outlined below.

5 g of neat sample was heated to 130° C. in a Sartorius MA 30 moisture analyser until a constant dry weight was achieved. From this a constant dry weight, % silica can be calculated. This was done on each aliquot and a comparison made. The results so far for Example 7a indicate that virtually no sedimentation has occurred at any of the testing conditions over 5 months.

The sedimentation times of Examples 1-11 after storage at room temperature are given below. Sedimentation times of less than 30 days were assessed by visual inspection. Sedimentation times of greater than 30 days were measured as described above.

| Example No. | 1 | 2 | 3 | 4 | 5 | 6 | 7a | 8 | 9 | 10 | 11 |
|---|---|---|---|---|---|---|---|---|---|---|---|
| Sedimentation Time (Days) | 2 | 5 | 2 | — | 5 | — | 150 | 60 | 1 | 7 | 90 |

BIOCIDAL ACTIVITY TEST

Aliquots (10 ml) of each sample (diluted where appropriate) were challenged with a 24 hour broth culture of *Streotococcus salivarius* NCIB 8883 to give a concentration of $10^5$–$10^6$ organisms per ml. Aliquots (1 ml) were withdrawn at intervals, diluted and pour plates made from 1 ml volumes of each. Colonies were counted following incubation of the plates at 37° C. for 2 days. Counts were carried out on the suspension of test organism to establish the inoculum level. Validation tests were carried out to identify those product dilutions where adequate neutralization of the actives had taken place and from which the number of survivors could be calculated.

Two compositions which were identical to Example 7a except that each contained a) 0.01, and b) 0.1% of bromochlorophene, respectively, were prepared as described for Example 7a. Each was tested undiluted in the above biocidal activity test. No difference could be detected in the biocidal activity of undiluted compositions a) and b) and the control which contained no bromochlorophene. All three effected a >4 log reduction within 30 seconds.

This test was repeated using 1/80 diluted compositions of a) and b) and control. An anti-plaque and an antiseptic mouthwash were also tested at 1/80 dilution as control mouthwashes. Again no difference was detected between a) and b) and the control. No anti-bacterial activity was detected in the two control mouthwash preparations against *S. salivarius* NCIB 8883. These results suggest that bromochlorophene alone is not responsible for the observed biocidal activity and that the mouthwash composition of Example 7a possesses surprisingly good antibacterial properties.

We claim:

1. An abrasive mouthwash composition which comprises
   a) 0.1 to 50% by weight of dentally acceptable abrasive;
   b) 0.01 to 5% by weight of synthetic or natural clay;
   c) 0.1 to 5% by weight of surfactant; and
   d) at least 45% of a liquid carrier,
in the form of a pourable suspension having a viscosity (Brookfield) of 1–2000 cps,
   said liquid carrier having an emulsion or micro-emulsion of levels of flavoring agents having a high flavor impact, and containing at least 5% by weight water, at least 5 percent by weight of humectant selected from the group consisting of glycerin, sorbitol, propylene glycol, polyethylene glycol and mixtures thereof, up to 5% by weight silicone oil, up to 35% by weight of alcohol, said clay suspending agent maintaining said solid abrasive particles in a substantially physically stable pourable mouthwash during storage, without overthickening, said pourable abrasive mouthwash having a mildly abrasive action on the teeth when rinsed around in the mouth, when used with or without a toothbrush, or as a pre- or post-brushing rinse with the toothbrush, said abrasive in said composition having an radioactive dentine abrasion value (RDA) of about 30 to 200.

2. An abrasive mouthwash composition according to claim 1 in which the dentally acceptable abrasive is selected from insoluble calcium salts, alumina, silica, synthetic resins and mixtures thereof.

3. An abrasive mouthwash composition according to claim 2 in which the surfactant is selected from anionic, nonionic and amphoteric surfactants and mixtures thereof.

4. An abrasive mouthwash composition according to claim 3 in which the liquid carrier comprises 5 to 35% of alcohol.

5. An abrasive mouthwash composition according to claim 4 which comprises an active ingredient having anti-plaque activity.

6. An abrasive mouthwash composition according to claim 5 which comprises at least one of a water insoluble anti-bacterial agent and a water insoluble anti-tartar agent.

7. An abrasive mouthwash according to claim 1 which comprises:
  a) 4 to 15% by weight of silica abrasive;
  b) 3.0 to 4.0% by weight of montmorillonite clay;
  c) 0.2 to 2.5% by weight of surfactant;
  d) 80 to 95% by weight of liquid carrier, and
  e) 0.2 to 1% by weight of flavouring, in the form of a pourable suspension having a viscosity (Brookfield) of 1 to 2000 cps.

8. An abrasive mouthwash according to claim 7 in which the surfactant is a higher alkyl sulphate.

9. An abrasive mouthwash according to claim 7 in which the liquid carrier comprises a mixture of water and 5-15% by weight of the composition of humectant.

10. A method of cleaning teeth comprising rinsing the mouth with a composition according to claim 1, expelling the bulk of the composition from the mouth, brushing the teeth with a toothbrush and finally re-rinsing the oral cavity with further composition or water.

11. An abrasive mouthwash composition according to claim 1 in which the clay concentration is 2 to 5% by weight and the viscosity is 20-1500 cps.

12. An abrasive mouthwash composition according to claim 11 in which the clay concentration is 3-4% and the viscosity is 100-1000 cps.

13. An abrasive mouthwash composition according to claim 12 in which the clay concentration is 3.3-3.7% and the viscosity is 200-600 cps.

14. An abrasive mouthwash composition according to claim 7 in which the clay concentration is 2 to 5% by weight and the viscosity is 20-1500 cps.

15. An abrasive mouthwash composition according to claim 14 in which the clay concentration is 3-4% and the viscosity is 20-1000 cps.

16. An abrasive mouthwash composition according to claim 15 in which the clay concentration is 3.3-3.7% and the viscosity is 200-600 cps.

17. An abrasive mouthwash according to claim 16 containing 0.001-1% by weight of water insoluble, non-ionic, anti-bacterial agent, 0.1-1% water insoluble anti-tartar agent and having a pH of about 3.5-9.

18. An abrasive mouthwash according to claim 17 in which the surfactant is a higher alkyl sulphate, the liquid carrier comprises a mixture of water and 5-15% by weight of the composition of humectant, 0.01-0.5% anti-bacterial agent and has a pH of about 5.5-8.

19. An abrasive mouthwash according to claim 1 which has a clear appearance.

20. An abrasive mouthwash composition according to claim 1 containing an anionic gum.

21. An abrasive mouthwash composition according to claim 20 in which the anionic gum is xanthan gum.

22. An abrasive mouthwash composition according to claim 20 in which the clay is a smectite clay.

23. An abrasive mouthwash composition according to claim 22 in which the anionic gum is xanthan gum and in which the mixture of xanthan gum and smectite clay is 0.1 to 1% by weight.

* * * * *